Feb. 19, 1963 A. D. CARTWRIGHT, SR Plant Pat. 2,229
ILEX CORNUTA PLANT (CHINESE HOLLY)
Filed April 10, 1962
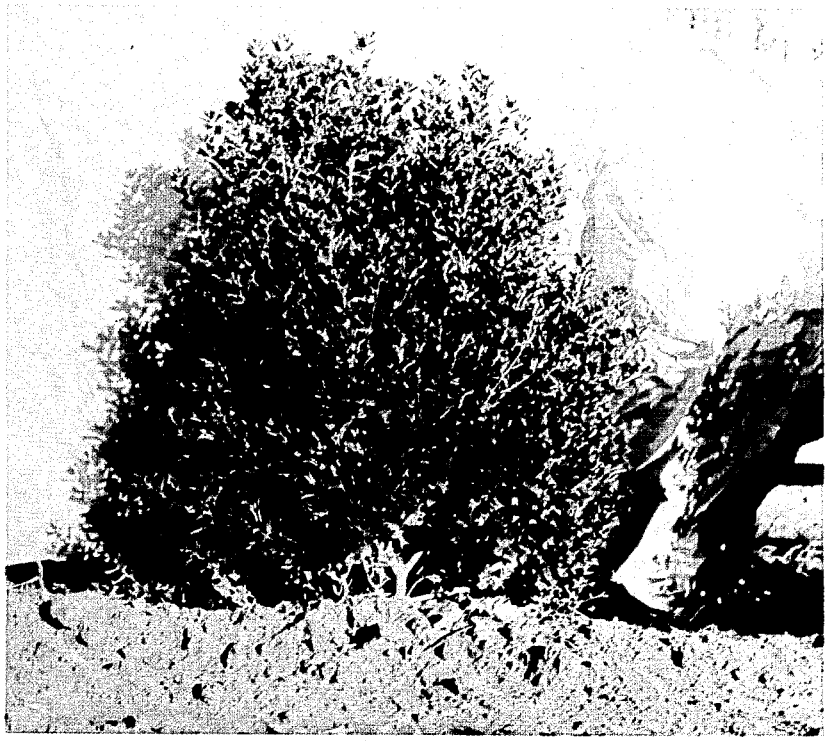
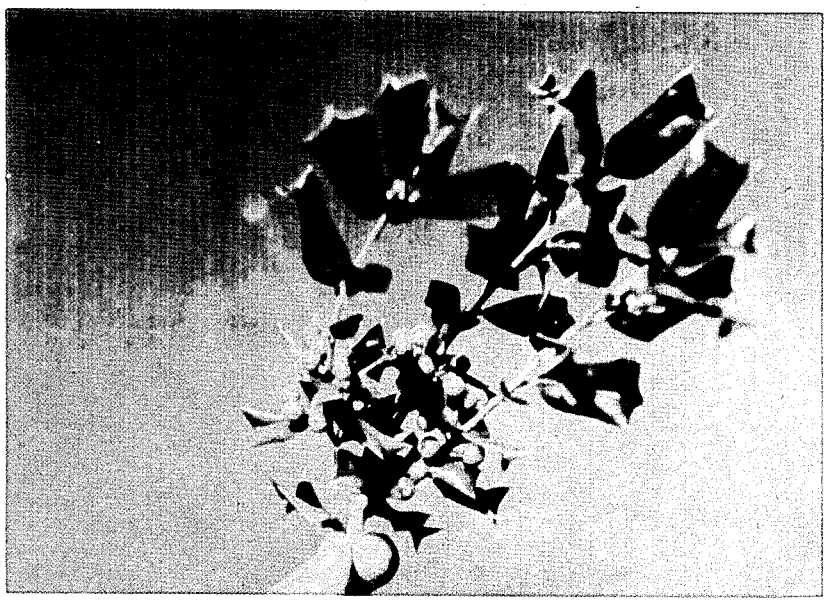
INVENTOR
ALBERT D. CARTWRIGHT, SR.
BY Lamont Johnston
ATTORNEY United States Patent Office Plant Pat. 2,229
Patented Feb. 19, 1963

2,229

ILEX CORNUTA PLANT (CHINESE HOLLY)

Albert D. Cartwright, Sr., Collierville, Tenn., assignor to Cartwright Nurseries, Collierville, Tenn., a partnership Filed Apr. 10, 1962, Ser. No. 186,565
1 Claim. (Cl. 47—59)

My invention relates to a new and distinct cultivar of Chinese holly plant or *Ilex cornuta*. The new plant originated as an open pollinated or chance seedling from plants of *Ilex cornuta* in my nursery at Collierville, Tennessee.

This new cultivar was selected for its ease in propagation, transplanting, and the following characteristics which are easily distinguished from other cultivars of *Ilex cornuta*:

(1) Small, rectangular, oblong, spiny, dark glossy, green leaves.

(2) Small red berries borne freely on young plants.

(3) Dense, broad upright habit of growth with foliage produced on short internodal branches.

(4) Adaptable to a wide range of soils and with persistent dark green foliage.

Asexual propagation of this new plant by cuttings, as performed in my nursery at Collierville, Tennessee, shows that this plant reproduces true to form with the above characteristics transmitted through succeeding propogations.

References to color in the following description refer to the Horticulture Colour Chart, volumes I and II, issued by the British Colour Council and the Royal Horticultural Society. Where there are other references to color, the ordinary dictionary meanings of the terms are intended.

The accompanying illustrations show in natural color a typical branch of foliage and berries, and the habit of growth of an entire plant.

*The Plant*

Growth habit: A dense broad upright evergreen plant; short internodes ⅜″–⅝″, lateral branchlets produced abundantly.

Foliage: Leaves—glabrous, rectangular oblong with 3 prominent spines of nearly equal length at the 3-spined apex, terminal spine reflexed; one spine on each side of the wide angular base; revolute translucent margin; alternate, coriaceous, thick dark lustrous green, 1″ to 1½″ long, ½″ to ⅝″ wide.

Color: Mature upper surface, glossy, Spinach Green o960; under side, Scheeles Green $860/_1$.

Flowers: Carpellate, usually borne in fascicles on previous season's growth, creamy white, April.

Fruit: Globose 3/16″ to ¼″ diameter. Stigma discoid and depressed, 3 to 5 in a cluster; pedicels short 3/16″ to ¼″ long. Fruit readily produced on young plants.

Color: Turkey Red $721/_1$.

Seed: Small 4; ⅛″ to 3/16″.

Disease and pest resistance: Highly resistant to diseases and insects, as observed under field conditions in my nursery and in comparison with other cultivars of *Ilex cornuta*.

Hardiness: Hardy without protection in zones 6*b*, 7, 8, 9, and 10, as shown in the Plant Hardiness Zone Map, Miscellaneous Publication #814. Agricultural Research Service, U.S.D.A. Additional hardiness zones to be determined in the future.

The disease and pest resistance has been demonstrated by growing this new cultivar in my nursery at Collierville, Tennessee, adjacent to other varieties of *Ilex cornuta*. While diseases are not too prevalent among *Ilex cornuta* varieties in general, this new cultivar has shown no indication of leaf spot, scale or chlorosis, while these conditions have, in some cases, been encountered in other varieties of *Ilex cornuta* grown nearby. As to hardiness, there has ben no winter damage or seasonal damage to plants of this new cultivar in my nursery during the last two seasons. The same observations as to disease resistance and hardiness have been made during the last two seasons by nurserymen growing this new cultivar on an experimental basis in the Memphis, St. Louis, and Philadelphia areas.

I claim:

A new and distinct cultivar of *Ilex cornuta* (Chinese holly) plant with combination of features herein shown and described, characterized particularly by the small, dark glossy green, rectangular oblong, spiny leaves and dense, broad, upright habit of growth.

No references cited.